United States Patent
Sakanishi et al.

(10) Patent No.: US 10,618,919 B2
(45) Date of Patent: Apr. 14, 2020

(54) THICKENING STABILIZER AND THICKENING STABILIZER COMPOSITION INCLUDING SAME

(71) Applicants: DAICEL CORPORATION, Osaka-shi, Osaka (JP); YAMAGUCHI UNIVERSITY, Yamaguchi-shi, Yamaguchi (JP)

(72) Inventors: Yuichi Sakanishi, Tokyo (JP); Takashi Saeki, Ube (JP); Aya Kaide, Ube (JP)

(73) Assignees: DAICEL CORPORATION, Osaka-shi (JP); YAMAGUCHI UNIVERSITY, Yamaguchi-shi (JP)

( * ) Notice: Subject to any disclaimer, the term of this patent is extended or adjusted under 35 U.S.C. 154(b) by 0 days.

(21) Appl. No.: 16/492,448

(22) PCT Filed: Mar. 2, 2018

(86) PCT No.: PCT/JP2018/007983
§ 371 (c)(1),
(2) Date: Sep. 9, 2019

(87) PCT Pub. No.: WO2018/163989
PCT Pub. Date: Sep. 13, 2018

(65) Prior Publication Data
US 2020/0040014 A1 Feb. 6, 2020

(30) Foreign Application Priority Data

Mar. 10, 2017 (JP) ................. 2017-045780

(51) Int. Cl.
*C07F 7/08* (2006.01)
(52) U.S. Cl.
CPC .......... *C07F 7/0803* (2013.01); *C07F 7/0838* (2013.01); *C07F 7/0872* (2013.01)

(58) Field of Classification Search
CPC ....... C07F 7/083; C07F 7/0838; C07F 7/0872
See application file for complete search history.

(56) References Cited

FOREIGN PATENT DOCUMENTS

| JP | 1-163111 A | 6/1989 |
|----|-----------|--------|
| JP | 2001207055 | * 7/2001 |

OTHER PUBLICATIONS

International Preliminary Report on Patentability and Written Opinion dated Sep. 19, 2019, in PCT JP/2018/007983.
International Search Report dated May 15, 2018, in PCT/JP2018/007983.

* cited by examiner

*Primary Examiner* — Jafar F Parsa
(74) *Attorney, Agent, or Firm* — Birch, Stewart, Kolasch & Birch, LLP

(57) ABSTRACT

The present invention provides a compound that thickens or gels a fluid organic substance to a desired viscosity, or uniformly stabilizes a composition containing a fluid organic substance. The compound of the present invention is a compound represented by Formula (1) below: wherein, $R^1$ represents a monovalent aliphatic hydrocarbon group having 4 or more carbons; $R^2$ represents a divalent aliphatic hydrocarbon group having from 1 to 12 carbons; $R^3$ represents a monovalent aliphatic hydrocarbon group having from 1 to 12 carbons; m represents an integer from 0 to 10; and n represents an integer from 1 to 4; in a case where n is 1 or 2, (4−n) $R^1$'s may be the same or different; and in a case where n is from 2 to 4, n $R^2$s, n $R^3$s, and n m's each may be the same or different.

4 Claims, No Drawings

THICKENING STABILIZER AND THICKENING STABILIZER COMPOSITION INCLUDING SAME

TECHNICAL FIELD

The present invention relates to a novel compound having an action of thickening and stabilizing fluid organic substances, such as oils; a thickening stabilizer including such a compound; and a composition including a fluid organic substance thickened and stabilized by the thickening stabilizer. The present application claims priority to JP 2017-045780 filed to Japan on Mar. 10, 2017, whose content is incorporated herein.

BACKGROUND ART

Methods of thickening and stabilizing liquids are industrially very important techniques. For example, mayonnaise and salad dressing, which are emulsions in metastable states, can stably maintain their emulsified state for a long period of time. This is because aqueous components therein are thickened and stabilized. Accordingly, various thickening stabilizers have been developed.

For example, alkyl acrylate copolymers are known as compounds that thicken and stabilize aqueous media.

On the other hand, 12-hydroxystearic acid is known as a thickening stabilizer for fluid organic substances (for example, organic substances having fluidity, such as oily media) (Patent Document 1, etc.). For its gelling action, 12-hydroxystearic acid is mainly used in disposal of edible oils. However, 12-hydroxystearic acid cannot control the degree of gelling, and it could only induce the oil either in a fully solidified state or still in a liquid state. Among the fluid organic substances, silicone oils, in particular, have low solubilities and thus have been very difficult to thicken or gel to a desired viscosity.

CITATION LIST

Patent Document

Patent Document 1: JP 01-163111 A

SUMMARY OF INVENTION

Technical Problem

Accordingly, an object of the present invention is to provide a compound that thickens or gels a fluid organic substance to a desired viscosity, or uniformly stabilizes a composition containing a fluid organic substance.

Another object of the present invention is to provide a thickening stabilizer containing the compound; a thickening stabilizer composition including a fluid organic substance thickened, gelled, or stabilized by the thickening stabilizer; and a method for manufacturing such a composition.

Solution to Problem

As a result of diligent study to solve the above problems, the present inventors found that a compound represented by Formula (1) below is capable of thickening or gelling a fluid organic substance, or uniformly stabilizing a composition containing a fluid organic substance (inhibiting sedimentation, local aggregation, or concentration of the composition, and maintaining a uniform state stably); and is capable of thickening or gelling a fluid organic substance such that the fluid organic substance has a desired viscosity, or uniformly stabilizing a composition containing a fluid organic substance, by selectively using the compound depending on the type of a fluid organic substance. The present invention has been completed based on these findings.

Specifically, the present invention provides a compound represented by Formula (1) below:

[Chemical Formula 1]

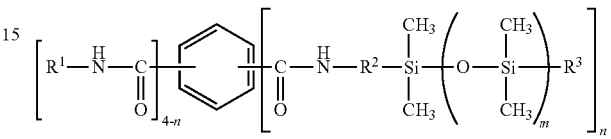

wherein, $R^1$ represents a monovalent aliphatic hydrocarbon group having 4 or more carbons; $R^2$ represents a divalent aliphatic hydrocarbon group having from 1 to 12 carbons; $R^3$ represents a monovalent aliphatic hydrocarbon group having from 1 to 12 carbons; m represents an integer from 0 to 10; and n represents an integer from 1 to 4; in a case where n is 1 or 2, (4−n) $R^1$s may be the same or different; and in a case where n is from 2 to 4, n $R^2$s, n $R^3$s, and n m's each may be the same or different.

The present invention also provides a thickening stabilizer including the compound.

The present invention also provides a thickening stabilizer composition including a miscible material of the thickening stabilizer and a fluid organic substance.

The present invention also provides a method for manufacturing a thickening stabilizer composition, the method including blending the thickening stabilizer and a fluid organic substance to make a miscible material to produce the thickening stabilizer composition.

Advantageous Effects of Invention

The compound represented by Formula (1) of the present invention, being blended with a fluid organic substance (particularly, a fluid organic substance including a silicone oil) to make a miscible material, can readily thicken or gel the fluid organic substance, or uniformly stabilize a composition containing the fluid organic substance. Thus, the compound, being added to a composition (such as, for example, cosmetics, paints, foods, and pharmaceuticals) including a fluid organic substance (particularly, a fluid organic substance including a silicone oil), can adjust the viscosity of the fluid organic substance to a desired range, and can maintain the make-up of the composition including the fluid organic substance uniformly, thereby improving the usability.

DESCRIPTION OF EMBODIMENTS

Compound Represented by Formula (1)

A compound according to an embodiment of the present invention is represented by Formula (1) below. In the formula, $R^1$ represents a monovalent aliphatic hydrocarbon group having 4 or more carbons; $R^2$ represents a divalent aliphatic hydrocarbon group having from 1 to 12 carbons; $R^3$ represents a monovalent aliphatic hydrocarbon group having from 1 to 12 carbons; m represents an integer from 0 to 10; and n represents an integer from 1 to 4; in a case where n is 1 or 2, (4−n) $R^1$s may be the same or different; and in a case where n is from 2 to 4, n units of $R^2$ may be the same or different, n units of $R^3$ may be the same or different, and n units of m may be the same or different.

[Chemical Formula 2]

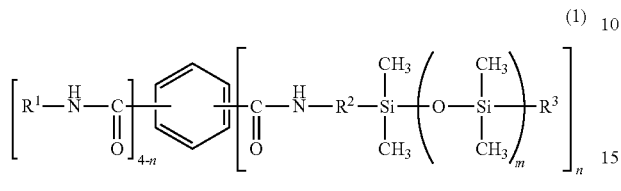
(1)

In the above formula, $R^1$ represents a monovalent aliphatic hydrocarbon group having 4 or more carbons, and examples thereof include: a linear or branched alkyl group having from approximately 4 to 20 (preferably from 4 to 18, and particularly preferably from 6 to 16) carbons, such as butyl, isobutyl, t-butyl, pentyl, hexyl, octyl, 2-ethylhexyl, decyl, lauryl, myristyl, stearyl, and nonadecyl groups; a linear or branched alkenyl group having from approximately 4 to 20 (preferably from 4 to 18, and particularly preferably from 6 to 16) carbons, such as 1-butenyl, 1-pentenyl, 2-hexenyl, 3-hexenyl, 4-hexenyl, 5-hexenyl, 7-octenyl, 9-decenyl, 11-dodecenyl, and oleyl groups; and a linear or branched alkynyl group having from approximately 4 to 20 (preferably from 4 to 18, and particularly preferably from 6 to 16) carbons, such as butynyl, pentynyl, hexynyl, octynyl, decynyl, pentadecynyl, and octadecynyl groups.

Among them, $R^1$ is preferably a linear or branched alkyl group and particularly preferably a linear alkyl group, having from 4 to 20 (preferably from 4 to 18, and particularly preferably from 6 to 16) carbons, in that they provide excellent solubility in fluid organic substances and can exhibit an effect of thickening fluid organic substances.

In the above formula, $R^2$ represents a divalent aliphatic hydrocarbon group having from 1 to 12 carbons, and examples thereof include a linear or branched alkylene group having from 1 to 12 carbons, such as a methylene group, a methylmethylene group, a dimethylmethylene group, an ethylene group, a propylene group, and a trimethylene group.

Among them, $R^2$ is preferably a linear or branched alkylene group and particularly preferably a linear alkylene group, having from 1 to 12 (preferably from 1 to 10, particularly preferably from 1 to 8, and most preferably from 1 to 5) carbons.

In the above formula, $R^3$ represents a monovalent aliphatic hydrocarbon group having from 1 to 12 carbons, and examples thereof include: an alkyl group having from approximately 1 to 12 (preferably from 1 to 5, and particularly preferably from 1 to 3) carbons, such as a methyl group, an ethyl group, a propyl group, an isopropyl group, a butyl group, an isobutyl group, an s-butyl group, a t-butyl group, a pentyl group, a hexyl group, a decyl group, and a dodecyl group; an alkenyl group having from approximately 2 to 12 (preferably from 2 to 10, and particularly preferably from 2 to 3) carbons, such as a vinyl group, an allyl group, and a 1-butenyl group; and an alkynyl group having from approximately 2 to 12 (preferably from 2 to 10, and particularly preferably from 2 to 3) carbons, such as an ethynyl group and a propynyl group.

Among them, $R^3$ is preferably a linear or branched alkyl group and particularly preferably a linear alkyl group, having from 1 to 12 (preferably from 1 to 10, particularly preferably from 1 to 8, and most preferably from 1 to 5) carbons.

Examples of the compound represented by Formula (1) above include compounds represented by Formulas (1-1) to (1-6) below. The group represented by the formula below:

[Chemical Formula 3]

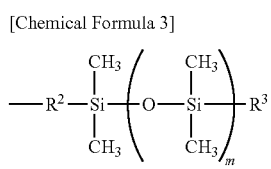

in Formula (1) is represented as $R^4$ in Formulas (1-1) to (1-6) below. Two $R^1$s and two $R^4$s each in Formulas (1-1) to (1-6) below may be the same or different.

[Chemical Formula 4]

(1-1)

(1-2)

(1-3)

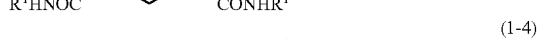
(1-4)

(1-5)

(1-6)

Among compounds represented by Formula (1) of an embodiment of the present invention, compounds represented by Formula (1-4) above are particularly preferred in that they have excellent solubility in fluid organic substances. The compounds represented by Formula (1-4) are also preferred in that the compounds can impart a fluid organic substance pseudoplastic behavior and strong storage modulus while maintaining transparency in a case where the fluid organic substance is transparent.

The compound represented by Formula (1) can be manufactured by, for example, methods described below.

1, A method of allowing a benzenetetracarboxylic acid to react with thionyl chloride to form a benzenetetracarboxylic acid tetrachloride, and allowing an amine (1) ($R^1$—$NH_2$) ($R^1$ is the same as described above) and an amine (2) ($R^4$—$NH_2$) ($R^4$ is the same as described above) to react with the resulting benzenetetracarboxylic acid tetrachloride 2, A method of allowing one of an amine (1) ($R^1$—$NH_2$) ($R^1$ is the same as described above) or an amine (2) ($R^4$—$NH_2$) ($R^4$ is the same as described above) to react with a benzenetetracarboxylic dianhydride to form an amic acid, and then further condensing the other one of the amines using a carbodiimide Among the benzenetetracarboxylic acids, 1,2,4,5-benzenetetracarboxylic acid can be suitably used.

Examples of the amine (1) ($R^1$—$NH_2$) include an amine having a linear or branched alkyl group (particularly, a linear alkyl group) having from 4 to 20 (preferably from 4 to 18, and particularly preferably from 6 to 16) carbons as $R^1$, such as hexylamine, octylamine, 2-ethylhexylamine, decylamine, laurylamine, myristylamine, stearylamine, and oleylamine.

The amine (2) ($R^4$—$NH_2$) is more particularly represented by Formula (2) below. In the formula below, $R^2$, $R^3$, and m are the same as described above.

[Chemical Formula 5]

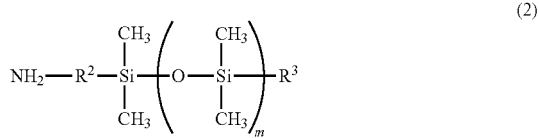

(2)

Examples of the amine (2) ($R^4$—$NH_2$) include 3-aminopropylpentamethyldisiloxane, 3-aminopropylheptamethyltrisiloxane, 3-aminopropylnonamethyltetrasiloxane, 3-aminopropylundecamethylpentasiloxane, 3-aminopropyltridecamethylhexasiloxane, 4-aminobutylpentamethyldisiloxane, 4-aminobutylheptamethyltrisiloxane, 4-aminobutylnonamethyltetrasiloxane, 4-aminobutylundecamethylpentasiloxane, 4-aminobutyltridecamethylhexasiloxane, 5-aminopentylpentamethyldisiloxane, 5-aminopentylheptamethyltrisiloxane, 5-aminopentylnonamethyltetrasiloxane, 5-aminopentylundecamethylpentasiloxane, and 5-aminopentyltridecamethylhexasiloxane.

In the manufacturing method 1 above, the reaction of the benzenetetracarboxylic acid tetrachloride and the amine can be performed, for example, by adding the benzenetetracarboxylic acid tetrachloride dropwise into a system charged with the amine.

The amine is used in an amount (sum of the amine (1) and the amine (2)), for example, approximately from 4 to 8 mol and preferably from 4 to 6 mol, relative to 1 mol of the benzenetetracarboxylic acid tetrachloride.

The ratio of the amine (1) to the amine (2) to be used (molar ratio of the former:the latter) can be adjusted as appropriate for the desired compound represented by Formula (1). That is, the adjustment of the ratio of the amine (1) to the amine (2) to be used can control the numbers of the (CONH—$R^1$) group and the (CONH—$R^4$) group in the resulting compound represented by Formula (1).

The reaction of the benzenetetracarboxylic acid tetrachloride and the amine can be performed in the presence or absence of a solvent. Examples of the solvent include saturated or unsaturated hydrocarbon solvents, such as pentane, hexane, heptane, octane, and petroleum ether; aromatic hydrocarbon-based solvents, such as benzene, toluene, and xylene; halogenated hydrocarbon-based solvents, such as methylene chloride, chloroform, 1,2-dichloroethane, chlorobenzene, and bromobenzene; ether-based solvents, such as diethyl ether, diisopropyl ether, dibutyl ether, tetrahydrofuran, dioxane, 1,2-dimethoxyethane, and cyclopentyl methyl ether; nitrile-based solvents, such as acetonitrile and benzonitrile; sulfoxide-based solvents, such as dimethyl sulfoxide; sulfolane-based solvents, such as sulfolane; amide-based solvents, such as dimethylformamide; high boiling point solvents, such as silicone oils. One type alone or two or more types thereof in combination can be used.

The solvent is used in an amount, for example, approximately from 50 to 300 wt. % relative to the total amount of the benzenetetracarboxylic acid tetrachloride and the amine. The solvent, when used in an amount greater than the above range, decreases concentrations of the reaction components, and tends to decrease the reaction rate.

The reaction of the benzenetetracarboxylic acid tetrachloride and the amine (=adding dropwise) is typically performed under normal pressure. In addition, the atmosphere of the above reaction (=during dropwise addition) is not particularly limited as long as it does not inhibit the reaction. For example, any of an air atmosphere, a nitrogen atmosphere, and an argon atmosphere may be used. The reaction temperature (=temperature during dropwise addition) is, for example, approximately from 30 to 60° C. The reaction time (=time of dropwise addition) is, for example, approximately from 0.5 to 20 hours. After completion of the reaction (=dropwise addition), an aging step may be provided. In a case where the aging step is provided, the aging temperature is, for example, approximately from 30 to 60° C., and the aging time is, for example, approximately from 1 to 5 hours. In addition, the reaction can be performed by any method, such as a batch method, a semi-batch method, and a continuous method.

After the completion of the reaction, the resulting reaction product can be separated and purified by a separation method, such as filtration, concentration, distillation, extraction, crystallization, adsorption, recrystallization, and column chromatography; and a separation means in combination thereof.

In the manufacturing method 2, the compound represented by Formula (1) can be manufactured, for example, by charging a benzenetetracarboxylic dianhydride, one of an amine (1) ($R^1$—$NH_2$) ($R^1$ is the same as described above) and an amine (2) ($R^4$—$NH_2$) ($R^4$ is the same as described above), and a solvent described below in the system, and age them to obtain an amic acid, and then charging the other one of the amines and an condensing agent (carbodiimide or salt thereof) to age them.

Among the benzenetetracarboxylic di anhydrides, 1,2,4, 5-benzenetetracarboxylic acid-1,2:4,5-dianhydride can be suitably used.

Examples of the amines (1) and (2) include the same as those used in the manufacturing method 1.

The amine (1) is used in an amount, for example, approximately from 2 to 4 mol and preferably from 2 to 3 mol, relative to 1 mol of the benzenetetracarboxylic dianhydride. In addition, the amine (2) is used in an amount, for example, approximately from 2 to 4 mol and preferably from 2 to 3 mol, relative to 1 mol of the benzenetetracarboxylic dianhydride.

The carbodiimide is represented by the following formula.

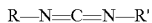

where R and R' are, for example, a linear or branched alkyl group having from 3 to 8 carbons or a 3- to 8-membered cycloalkyl group, which may have a hetero atom-containing substituent, R and R' may be the same or different, and R and R' may also be bonded to each other to form a ring together with a group (—N=C=N—).

Examples of the linear or branched alkyl group having from 3 to 8 carbons include propyl, isopropyl, butyl, isobutyl, s-butyl, t-butyl, pentyl, isopentyl, s-pentyl, t-pentyl, hexyl, isohexyl, s-hexyl, and t-hexyl groups.

Examples of the 3- to 8-membered cycloalkyl group include cyclopropyl, cyclobutyl, cyclopentyl, cyclohexyl, and cyclooctyl groups.

Examples of the heteroatom-containing substituent include nitrogen atom-containing substituents, such as an amino group and di($C_{1-3}$)alkylamino groups such as a dimethylamino group.

Examples of the carbodiimides include diisopropylcarbodiimide, dicyclohexylcarbodiimide, and N-(3-dimethylaminopropyl)-N-ethylcarbodiimide. In addition, examples of the salt of carbodiimide include hydrochloride salts (specifically, such as N-(3-dimethylaminopropyl)-N-ethylcarbodiimide hydrochloride). One type alone or two or more types thereof in combination can be used.

The carbodiimide is used in an amount, for example, approximately from 2 to 6 mol and preferably from 2 to 4 mol, relative to 1 mol of the benzenetetracarboxylic dianhydride.

The solvent for use herein is preferably a proton-acceptor solvent having excellent solubility of the amic acid, for example, alcohols, such as methanol, ethanol, and isobutanol; hydrocarbons, such as hexane and cyclohexane; and mixtures thereof. One type alone or two or more types thereof in a mixture can be used.

The solvent is used in an amount, for example, approximately from 50 to 300 wt. % and preferably from 100 to 250 wt. %, relative to the total amount of the amic acid. The solvent, when used in an amount greater than the above range, decreases concentrations of the reaction components, and tends to decrease the reaction rate.

The above reaction is typically performed under normal pressure. In addition, the atmosphere of the above reaction is not particularly limited as long as it does not inhibit the reaction. For example, any of an air atmosphere, a nitrogen atmosphere, and an argon atmosphere may be used. The aging temperature (reaction temperature) is, for example, approximately from 25 to 70° C. The aging time of the benzenetetracarboxylic dianhydride and the amine is, for example, approximately from 0.5 to 5 hours, and the aging time of the amic acid and the amine is, for example, approximately from 0.5 to 20 hours. In addition, the reaction can be performed by any method, such as a batch method, a semi-batch method, and a continuous method.

After the completion of the reaction, the resulting reaction product can be separated and purified by a separation method, such as filtration, concentration, distillation, extraction, crystallization, adsorption, recrystallization, and column chromatography; and a separation method in combination thereof.

The compound represented by Formula (1) can self-associate through hydrogen bonding at the amide bond sites to form a fibrous self-assembly. Furthermore, the $R^1$ group has affinity for a fluid organic substance (particularly, a hydrocarbon oil described later), and the $R^4$ group has affinity for a fluid organic substance (particularly, a silicone oil described later). Thus, the compound, making a miscible material with a fluid organic substance, can thicken or gel the fluid organic substance, or uniformly stabilize a composition containing the fluid organic substance.

Still further, the compound represented by Formula (1) includes the $R^1$ and $R^4$ groups different from each other, and thus has moderate crystallinity. As a result, the compound can thicken and stabilize a fluid organic substance without particular limitation. Furthermore, in a case where the fluid organic substance has transparency, the compound can thicken and stabilize the substance while maintaining the transparency to form a thickening stabilizer composition that is stable over time. Thus, the compound is useful, for example, as a thickening stabilizer (more particularly, a thickener, a gelling agent, or a stabilizer) for fluid organic substances. On the other hand, in the case where the $R^1$ and $R^4$ groups in the compound represented by Formula (1) represent the same groups (that is, in the case where the compound represented by Formula (1) has four identical groups as side chains), the crystallinity becomes too high. Thus, there may be a limitation in ranges of fluid organic substances that can be thickened and stabilized. In addition, such a compound often causes white turbidity by thickening and stabilizing, and may impair the appearance. Furthermore, the viscosity also tends to decrease over time.

Thickening Stabilizer

The thickening stabilizer of an embodiment of the present invention includes one type of the compounds represented by Formula (1) above alone or two or more types thereof in combination.

In an embodiment of the present invention, a "thickening stabilizer" is a compound that is dissolved in a fluid organic substance to make the material viscous, and, in concept, includes a thickener, which imparts viscosity to a fluid organic substance, a gelling agent, which gels a fluid organic substance, and a stabilizer, which increases the viscosity, for the purpose of uniformly stabilizing a composition that includes a fluid organic substance.

In addition to the compound represented by Formula (1) above, the thickening stabilizer of an embodiment of the present invention may also contain other component(s) as necessary (for example, a base material; hydroxy fatty acids; an acrylic polymer; oligomer esters, such as a dextrin fatty acid ester; or particles, such as those of a metal oxide). The thickening stabilizer includes the other component(s) within a range such that the content (total amount in the case where the thickening stabilizer includes two or more types) of the compound represented by Formula (1) above is, for example, 0.5 wt. % or greater, preferably 1 wt. % or greater, more preferably 10 wt. % or greater, still more preferably 30 wt. % or greater, particularly preferably 60 wt. % or greater, and most preferably 85 wt. % or greater, in the total amount of the thickening stabilizer (100 wt. %). The upper limit of the content of the compound represented by Formula (1) above is 100 wt. %. The compound represented by Formula (1) above, when included in an amount outside the above range, tends to have difficulty in thickening or gelling a fluid organic substance, or uniformly stabilizing a composition containing a fluid organic substance.

Various types of agent forms, such as, for example, a powder form, a granular form, a liquid form, and an emulsion form, can be employed for the thickening stabilizer of an embodiment of the present invention.

The thickening stabilizer of an embodiment of the present invention, making a miscible material with a fluid organic substance (preferably mixed and warmed to make a miscible material, and then cooled), can thicken or gel the fluid organic substance, and can thicken or gel. The thickening stabilizer can thicken or gel the fluid organic substance to a desired viscosity, depending on an application, in a range from more than one-fold to about not greater than 600-fold (preferably from 5 to 600-fold).

Thickening Stabilizer Composition

The composition of an embodiment of the present invention includes a composition including a miscible material of the above thickening stabilizer and the thickening stabilizer fluid organic substance, i.e., a composition formed by thickening or gelling the fluid organic substance, or uniformly stabilizing a composition containing a fluid organic substance by the thickening stabilizer.

The thickening stabilizer composition can be manufactured via a step of blending the thickening stabilizer and a fluid organic substance to make a miscible material. More specifically, the thickening stabilizer composition can be manufactured by mixing and warming the total amount of the fluid organic substance and the thickening stabilizer to make a miscible material, and then cooling the miscible material. The thickening stabilizer composition can be also manufactured by a method of mixing the thickening stabilizer in a portion of the fluid organic substance, warming the mixture to make a miscible material, and then cooling the material to produce a thickening stabilizer composition, and mixing this composition in the remaining fluid organic substance.

The fluid organic substance is an organic substance having a viscosity of less than 0.1 Pa·s measured by a rheometer [viscosity ($\eta$) at 25° C. and a shear rate of 10 (1/s)], and examples thereof include hydrocarbon oils (such as hexane, cyclohexane, isododecane, benzene, toluene, poly-$\alpha$-olefins, and liquid paraffins), ethers (such as tetrahydrofuran), halogenated hydrocarbons (such as carbon tetrachloride and chlorobenzenes), petroleum components (such as kerosene, gasoline, light oil, and heavy oil), animal and vegetable oils (such as sunflower oils, olive oils, soybean oils, corn oils, castor oils, beef tallows, jojoba oils, and squalanes), silicone oils (such as dimethylpolysiloxanes, methylphenylpolysiloxanes, and decamethylcyclopentasiloxanes), esters (such as octyldodecyl oleate, cetyl octanoate, cetyl ethylhexanoate, glyceryl triisooctanoate, and neopentyl glycol diisooctanoate), aromatic carboxylic acids, and pyridine. One type alone or two or more types thereof in combination can be used.

Among the fluid organic substances in the present invention, at least a hydrocarbon oil and/or a silicone oil are preferably included, and in particular, a hydrocarbon oil and/or a silicone oil are included preferably in greater than 50 wt. % (particularly preferably in 60 wt. % or greater, and most preferably in 65 wt. % or greater) of the total amount of the fluid organic substance.

Among the fluid organic substances in the present invention, at least a silicone oil is preferably included, and a silicone oil is included preferably in greater than 50 wt. % (particularly preferably in 60 wt. % or greater, and most preferably in 65 wt. % or greater) of the total amount of the fluid organic substance.

The thickening stabilizer may be mixed (or used) in an amount, for example, from 0.1 to 100 parts by weight, preferably from 0.5 to 90 parts by weight, particularly preferably from 1 to 80 parts by weight, and most preferably from 1 to 30 parts by weight, relative to 1000 parts by weight of the fluid organic substance, although the amount depends on the type of the fluid organic substance. The thickening stabilizer, mixed (or used) in the above range, can provide a composition in which the fluid organic substance is thickened or gelled, or a composition in which the make-up is uniformly stabilized.

In addition to the above thickening stabilizer and the fluid organic substance, the thickening stabilizer composition of an embodiment of the present invention may include other component(s) within a range that does not impair the effects of an embodiment of the present invention. Examples of the other component(s) include common compounds (such as, for example, medicinal ingredients, pigments, and perfumes) included in compositions desired to be thickening stabilizer, such as cosmetics, paints, foods, and pharmaceuticals.

The temperature during the making a miscible material is selected as appropriate for the types of the thickening stabilizer and the fluid organic substance used, and is not particularly limited as long as it is a temperature at which the thickening stabilizer and the fluid organic substance are miscible. The temperature is preferably not higher than 100° C., and in a case where the boiling point of the fluid organic substance is 100° C. or lower, the temperature is preferably around the boiling point.

The cooling after the making the miscible material may be performed in any manner, as long as it is capable of cooling to 25° C. or lower, and it may be performed by a gradual cooling at room temperature or a rapid cooling, such as ice cooling.

The viscosity of the thickening stabilizer composition of an embodiment of the present invention measured by a rheometer [viscosity (ii) at 25° C. and a shear rate of 10 (1/s)] can be adjusted as appropriate for the application within a range of greater than 1 fold to not greater than 600-fold (preferably from 5 to 600-fold) of the viscosity of the fluid organic substance as a raw material.

The thickening stabilizer composition of an embodiment of the present invention is not particularly limited as long as being a composition containing a fluid organic substance and being desired to be thickening stabilizer. Examples thereof include cosmetics, paints, foods, and pharmaceuticals.

EXAMPLES

Hereinafter, the present invention will be described more specifically with reference to examples, however, the present invention is not limited by these examples.

Synthesis Example 1 [Synthesis of Thickening Stabilizer (1)]

To a 150-mL four-neck separable flask equipped with a Dimroth condenser, a nitrogen inlet, a dropping funnel, and a thermocouple, 2 g of isobutanol, 16 g of cyclohexane, and 532 mg (2.4 mmol) of 1,2,4,5-benzenetetracarboxylic acid-1,2:4,5-dianhydride were charged and mixed at a temperature in the system set at 25° C.

Next, 1.0 g (4.8 mmol) of 3-aminopropylpentamethyldisiloxane, as a raw material amine, was added dropwise over 5 minutes and allowed to stand for aging for 2 hours. Thereafter, 617 mg (4.8 mmol) of diisopropylcarbodiimide was charged to the flask over 5 minutes and aged for 10 minutes, then 629 mg (4.8 mmol) of octylamine was added dropwise over 10 minutes and aged at 25° C. for 2 hours, and then aged at 40° C. for 18 hours.

After removing solvents under reduced pressure, a precipitated solid was separated by filtration to yield 15 g of a crude product. This was washed with 20 g of acetone and separated by chromatography to yield a mixture (200 mg) of two types of compounds represented by the following formulas. The structures of the reaction products were identified by ¹H-NMR.

[Chemical Formula 6]

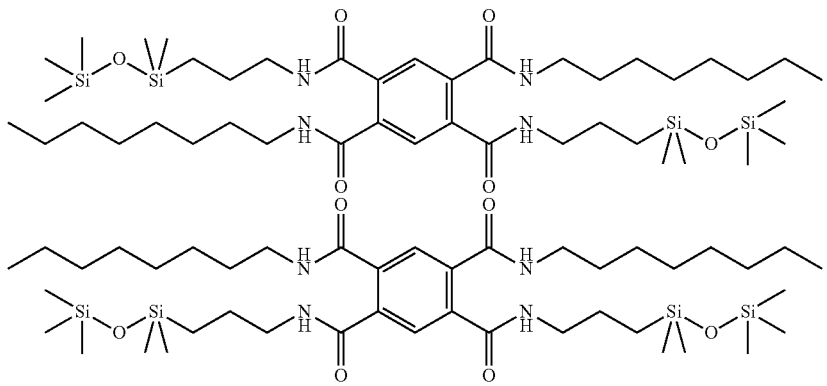

¹H-NMR (400 MHz, CDCl₃): δ 8.5-9.5 (m, 2H), 3.41-3.45 (m, 8H), 1.10-1.82 (m, 28H), 0.80-0.91 (m, 6H), 0.41-0.60 (m, 4H), 0.01-0.12 (m, 30H).

Synthesis Example 2 [Thickening Stabilizer (2)]

A mixture of two types of compounds represented by the following formulas was obtained in the same manner as in Synthesis Example 1 except for changing from 3-aminopropylpentamethyldisiloxane to 3-aminopropylundecamethylpentasiloxane.

[Chemical Formula 7]

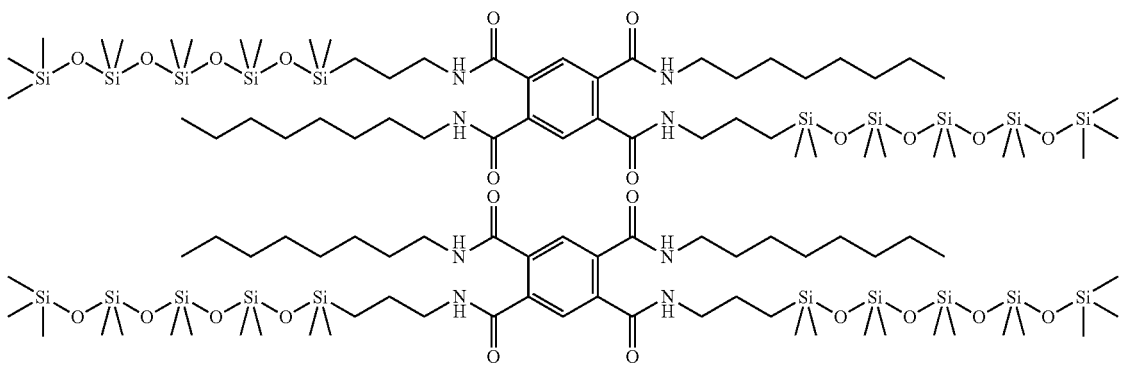

¹H-NMR (400 MHz, CDCl₃): δ 8.5-9.5 (m, 2H), 3.21-3.45 (m, 8H), 1.10-1.82 (m, 28H), 0.80-0.91 (m, 6H), 0.51-0.70 (m, 4H), 0.11-0.19 (m, 75H).

Synthesis Example 3 [Synthesis of Thickening Stabilizer (3)]

A mixture of two types of compounds represented by the following formulas was obtained in the same manner as in Synthesis Example 1 except for changing from 3-aminopropylpentamethyldisiloxane to 3-aminopropylundecamethylpentasiloxane and changing from octylamine to dodecylamine.

[Chemical Formula 8]

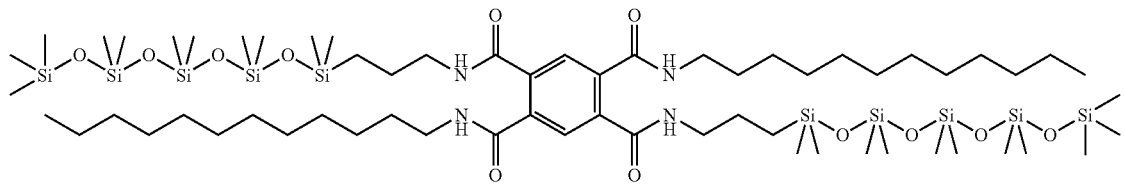

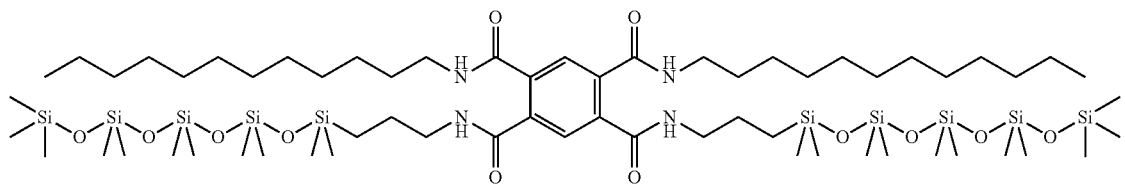

¹H-NMR (400 MHz, CDCl₃): δ 8.5-9.5 (m, 2H), 3.21-3.45 (m, 8H), 1.10-1.82 (m, 44H), 0.80-0.91 (m, 6H), 0.51-0.70 (m, 4H), 0.11-0.19 (m, 75H).

Synthesis Example 4 [Synthesis of Thickening Stabilizer (4) (1,2,4,5-benzene tetracarboxylic acid di-2-ethylhexylamide dioleylamide)]

To a 100-mL four-neck separable flask equipped with a Dimroth condenser, a nitrogen inlet, a dropping funnel, and a thermocouple, 20 mL of pyridine, 3.0 g (0.014 mol) of 1,2,4,5-benzenetetracarboxylic acid-1,2:4,5-dianhydride, and 7.4 g (0.028 mol) of oleylamine were charged. The temperature in the system was set at 50° C. and aged for 3 hours.
Thereafter, 3.6 g (0.028 mol) of 2-ethylhexylamine and 7.0 g (0.056 mol) of diisopropylcarbodiimide were charged and aged for another 8 hours.
A low-boiling component in the resulting crude liquid was removed by an evaporator and washed with methanol to yield a pale yellow wet powder. The resulting wet powder was further recrystallized with CHCl₃/CH₃OH (70/30 (v/v)) and 5.9 g of a mixture of two types of compounds represented by the following formulas [a mixture of 1,2,4,5-benzenetetracarboxylic acid-1,4-di(2-ethylhexylamide)-2,5-di(oleylamide) and 1,2,4,5-benzenetetracarboxylic acid-1,5-di(2-ethylhexylamide)-2,4-di(oleylamide)] (Yield: 51%) was obtained.

¹H-NMR (270 MHz, CDCl₃): δ 0.81-1.02 (m, 18H), 1.03-1.85 (m, 74H), 1.96-2.04 (m, 8H), 3.25-3.40 (m, 4H), 5.22-5.51 (m, 4H), 8.5-9.5 (m, 2H)

FAB-MS m/z: 973 (Calcd for $C_{62}H_{110}N_4O_4$: 974)

Synthesis Example 5 [Synthesis of Thickening Stabilizer (5) (1,2,4,5-benzenetetracarboxylic acid di-2-ethylhexylamide distearylamide)]

In the same manner as in Synthesis Example 4 except for changing from 7.4 g (0.028 mol) of oleylamine to 7.5 g (0.028 mol) of stearylamine, 5.1 g of a mixture of two types of compounds represented by the following formulas [a mixture of 1,2,4,5-benzenetetracarboxylic acid-1,4-di(2-ethylhexylamide)-2,5-di(stearylamide) and 1,2,4,5-benzenetetracarboxylic acid-1,5-di(2-ethylhexylamide)-2,4-di(stearylamide)] was obtained (Yield: 53%).

[Chemical Formula 9]

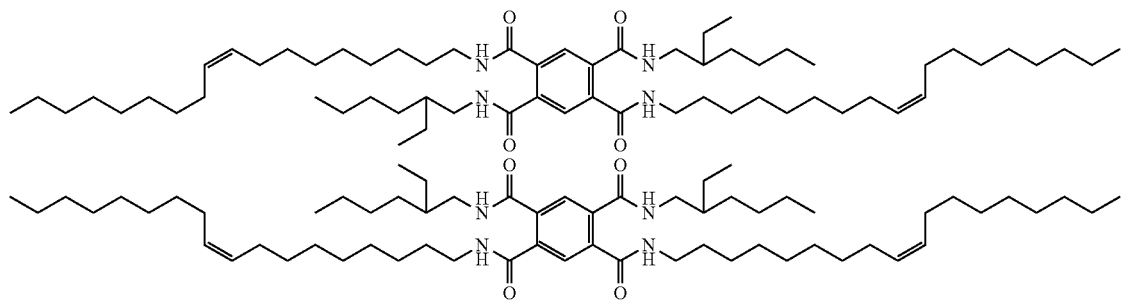

[Chemical Formula 10]

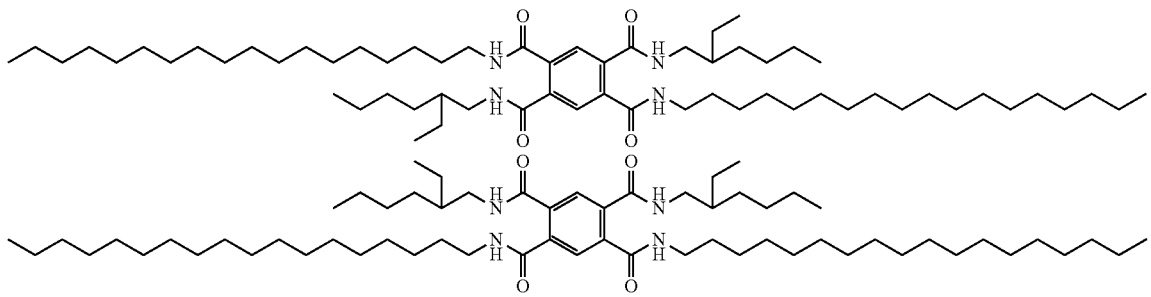

$^1$H-NMR (270 MHz, CDCl$_3$): δ 0.81-1.10 (m, 18H), 1.10-1.94 (m, 90H), 3.25-3.40 (m, 4H), 8.5-9.5 (m, 2H)

FAB-MS m/z: 977 (Calcd for C$_{62}$H$_{114}$N$_4$O$_4$: 978)

Example 1

To a test tube, 1 cm$^3$ each of various fluid organic substances shown in Table 1 (decamethylcyclopentasiloxane (hereinafter, it may be referred to as "D$_5$") or a mixed solution of D$_5$ and isododecane (hereinafter, it may be referred to as "ISD") (volume ratio=70/30)) was transferred, and 10 mg each of the thickening stabilizer (1) obtained in Synthesis Example 1 above was added and mixed, and heated and stirred at 100° C. to make the fluid organic substance and the thickening stabilizer miscible, and cooled to 25° C. to obtain a thickening stabilizer composition.

Examples 2 and 3, Comparative Examples 1 and 2

A thickening stabilizer composition was obtained in the same manner as in Example 1 except for using, as a thickening stabilizer, the thickening stabilizer (2) in Example 2, the thickening stabilizer (3) in Example 3, the thickening stabilizer (4) in Comparative Example 1, and the thickening stabilizer (5) in Comparative Example 2, instead of the thickening stabilizer (1).

Evaluation of Thickening Effect

Viscosity was measured for the thickening stabilizer compositions obtained in the examples and the comparative examples, and it was determined how many times the viscosities of the various fluid organic substances were increased to evaluate the thickening effect according to the following criteria.

Evaluation Criteria
 1: greater than 1.0 time and 2.0 times or less
 2: greater than 2.0 times and 4.8 times or less
 3: greater than 4.8 times and 10 times or less
 4: greater than 10 times and 50 times or less
 5: greater than 50 times and 100 times or less
 6: greater than 100 times and 10000 times or less The viscosities of the thickening stabilizer compositions were determined as follows. The measurement was performed using a viscosity/visco-elasticity measuring apparatus (rheometer) (trade name "RheoStress 600" available from HAAKE) equipped with a cone-plate sensor (a diameter of 60 mm with a cone angle of 1°, and a diameter of 35 mm with a cone angle of 1°, 2°, and 4° were used) and a Peltier temperature controller. The viscosities were measured in a steady flow viscosity measurement mode at 25° C. and different shear rates varied in a log scale from 0.001 to 100 (1/s) to obtain a viscosity curve. A viscosity at a shear rate of 10 (1/s) was determined from the obtained viscosity curve, and this was defined as the viscosity in the present invention. In each plot, a value was recorded when the torque value variation of the apparatus was settled within the range of 5% and the data became stable.

TABLE 1

| | | Example 1 | Example 2 | Example 3 | Comparative Example 1 | Comparative Example 2 |
|---|---|---|---|---|---|---|
| Fluid organic substances | D$_5$ | 6 | 6 | 6 | Not dissolved | Not dissolved |
| | D$_5$/ISD = 70/30 | 6 | 6 | 6 | 6 | 6 |

Table 1 above shows that the thickening stabilizer of the present invention has excellent thickening effect on a fluid organic substance including a silicone oil. On the other hand, the thickening stabilizers obtained in the comparative examples were not dissolved in a fluid organic substance including a silicone oil, and failed to exhibit the effect of thickening a fluid organic substance including a silicone oil.

To summarize the above, configurations of the present invention and variations thereof will be described below.

[1] A compound represented by Formula (1) below:

[Chemical Formula 1]

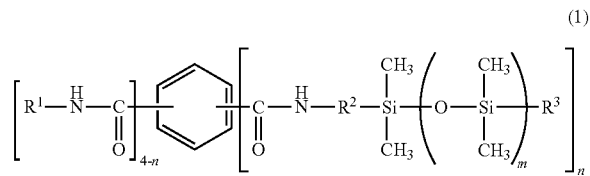

(1)

wherein, R$^1$ represents a monovalent aliphatic hydrocarbon group having 4 or more carbons; R$^2$ represents a divalent aliphatic hydrocarbon group having from 1 to 12 carbons; R$^3$ represents a monovalent aliphatic hydrocarbon group having from 1 to 12 carbons; m represents an integer from 0 to 10; and n represents an integer from 1 to 4; when n is 1 or 2, (4−n) $R^1$s may be the same or different; and when n is from 2 to 4, n $R^2$s, n $R^3$s, and n m's each may be the same or different.

[2] The compound according to [1], wherein $R^1$ is a linear or branched alkyl group, alkenyl group, or alkynyl group having from 4 to 20, from 4 to 18, or from 6 to 16 carbons.

[3] The compound according to [1] or [2], wherein $R^1$ is selected from the group consisting of a butyl group, an isobutyl group, a t-butyl group, a pentyl group, a hexyl group, an octyl group, a 2-ethylhexyl group, a decyl group, a lauryl group, a myristyl group, a stearyl group, a nonadecyl group, a 1-butenyl group, a 1-pentenyl group, a 2-hexenyl group, a 3-hexenyl group, a 4-hexenyl group, a 5-hexenyl group, a 7-octenyl group, a 9-decenyl group, an 11-dodecenyl group, an oleyl group, a butynyl group, a pentynyl group, a hexynyl group, an octynyl group, a decynyl group, a pentadecynyl group, and an octadecynyl group.

[4] The compound according to any one of [1] to [3], wherein $R^2$ is a linear or branched alkylene group having from 1 to 12, from 1 to 10, from 1 to 8, or from 1 to 5 carbons.

[5] The compound according to any one of [1] to [4], wherein $R^2$ is selected from the group consisting of a methylene group, a methylmethylene group, a dimethylmethylene group, an ethylene group, a propylene group, and a trimethylene group.

[6] The compound according to any one of [1] to [5], wherein $R^3$ is a linear or branched alkyl group having from 1 to 12, from 1 to 10, from 1 to 8, or from 1 to 5 carbons.

[7] The compound according to any one of [1] to [6], wherein $R^3$ is selected from the group consisting of a methyl group, an ethyl group, a propyl group, an isopropyl group, a butyl group, an isobutyl group, an s-butyl group, a t-butyl group, a pentyl group, a hexyl group, a decyl group, a dodecyl group, a vinyl group, an allyl group, a 1-butenyl group, an ethynyl group, and a propynyl group.

[8] The compound according to any one of [1] to [7], wherein the compound is a compound selected from the group consisting of compounds represented by Formulas (1-1) to (1-6) below:

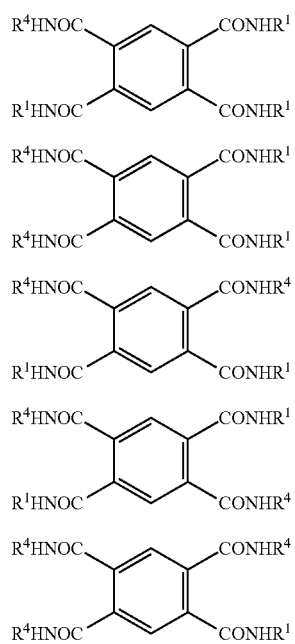

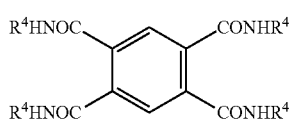

where $R^4$ is

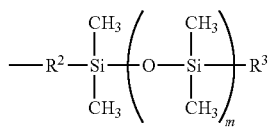

[9] The compound according to any one of [1] to [8], wherein the compound is manufactured by a method 1 of allowing a benzenetetracarboxylic acid to react with thionyl chloride to form a benzenetetracarboxylic acid tetrachloride, and allowing an amine (1) ($R^1$—$NH_2$) ($R^1$ is the same as described above) and an amine (2) ($R^4$—$NH_2$) ($R^4$ is the same as described above), to react with the resulting benzenetetracarboxylic acid tetrachloride.

[10] The compound according to any one of [1] to [9], wherein the compound is manufactured by a method 2 of allowing one of an amine (1) ($R^1$—$NH_2$) ($R^1$ is the same as described above) and an amine (2) ($R^4$—$NH_2$) ($R^4$ is the same as described above) to react with a benzenetetracarboxylic dianhydride to form an amic acid, and further condensing the other one of the amines using a carbodiimide.

[11] A thickening stabilizer including the compound described in any one of [1] to [10].

[12] Thickening stabilizer according to [11], further containing other component(s) selected from the group consisting of a base material, hydroxy fatty acids, an acrylic polymer, a dextrin fatty acid ester, or particles of a metal oxide, wherein the compound described in any one of [1] to [10] is included in an amount of 0.5 wt. % or greater, 1 wt. % or greater, 10 wt. % or greater, 30 wt. % or greater, 60 wt. % or greater, or 85 wt. % or greater, in the total amount of the thickening stabilizer (100 wt. %).

[13] The thickening stabilizer according to [11] or [12], wherein an agent form is selected from a powder form, a granular form, a liquid form, or an emulsion form.

[14] A thickening stabilizer composition including a miscible material of the thickening stabilizer described in any one of [11] to [13] and a fluid organic substance.

[15] The thickening stabilizer composition according to [14], wherein the fluid organic substance is an organic substance having a viscosity of less than 0.1 Pa·s measured by a rheometer [viscosity (η) at 25° C. and a shear rate of 10 (1/s)], and the fluid organic substance is selected from the group consisting of hydrocarbon oils, hexane, cyclohexane, isododecane, benzene, toluene, poly-α-olefins, liquid paraffins, ethers, tetrahydrofuran, halogenated hydrocarbons, carbon tetrachloride, chlorobenzenes, petroleum components, kerosene, gasoline, light oil, heavy oil, animal and vegetable oils, sunflower oils, olive oils, soybean oils, corn oils, castor oils, beef tallows, jojoba oils, squalanes, silicone oils, dimethylpolysiloxanes, methylphenylpolysiloxanes, decamethylcyclopentasiloxanes, esters, octyldodecyl oleate, cetyl octanoate, cetyl ethylhexanoate, glyceryl triisooctanoate, neopentyl glycol diisooctanoate, aromatic carboxylic acids, and pyridine.

[16] The thickening stabilizer composition according to [14] or [15], containing a hydrocarbon oil and/or a silicone oil in an amount of greater than 50 wt. %, 60 wt. % or greater, or 65 wt. % or greater of the total amount of the fluid organic substance.

[17] The thickening stabilizer composition according to any one of [14] to [16], wherein the thickening stabilizer is mixed (or used) in an amount from 0.1 to 100 parts by weight, from 0.5 to 90 parts by weight, from 1 to 80 parts by weight, or from 1 to 30 parts by weight, relative to 1000 parts by weight of the fluid organic substance.

[18] The thickening stabilizer composition according to any one of [14] to [17], wherein the viscosity measured by a rheometer [viscosity ($\eta$) at 25° C. and a shear rate of 10 (1/s)] is within a range of greater than 1- to 600-fold or less, or from 5- to 600-fold of the viscosity of the fluid organic substance as a raw material.

[19] The thickening stabilizer composition according to any one of [14] to [18], further including a medicinal ingredient, a pigment, or a perfume as the other component(s) other than the thickening stabilizer and the fluid organic substance.

[20] A method for manufacturing a thickening stabilizer composition, the method including blending the thickening stabilizer described in any one of [11] to [13] and a fluid organic substance to make a miscible material to form the thickening stabilizer composition.

[21] The method for manufacturing a thickening stabilizer composition according to [20], wherein the temperature during the making the miscible material is a temperature at which the thickening stabilizer and the fluid organic substance are miscible, and not higher than 100° C., or around the boiling point of the fluid organic substance.

[22] The method for manufacturing a thickening stabilizer composition according to [20] or [21], wherein the cooling after the making the miscible material is a cooling to 25° C. or lower, and is achieved by gradually cooling at room temperature or rapidly cooling by ice cooling.

INDUSTRIAL APPLICABILITY

The compound represented by Formula (1) of the present invention, being blended with a fluid organic substance (particularly, a fluid organic substance including a silicone oil) to make a miscible material, can readily thicken or gel the fluid organic substance, or uniformly stabilize a composition containing the fluid organic substance. Thus, the compound, being added to a composition (such as, for example, cosmetics, paints, foods, and pharmaceuticals) including a fluid organic substance (particularly, a fluid organic substance including a silicone oil), can adjust the viscosity of the fluid organic substance to a desired range, and can maintain the make-up of the composition including the fluid organic substance uniformly, thereby improving the usability.

The invention claimed is:

1. A compound represented by Formula (1):

[Chemical Formula 1]

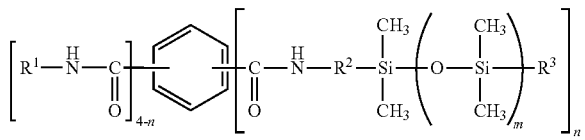

wherein, $R^1$ represents a monovalent aliphatic hydrocarbon group having 4 or more carbons; $R^2$ represents a divalent aliphatic hydrocarbon group having from 1 to 12 carbons; $R^3$ represents a monovalent aliphatic hydrocarbon group having from 1 to 12 carbons; m represents an integer from 0 to 10; and n represents an integer from 1 to 4; in a case where n is 1 or 2, (4−n) $R^1$s may be the same or different; and in a case where n is from 2 to 4, n $R^2$s, n $R^3$s, and n m's each may be the same or different.

2. A thickening stabilizer comprising the compound described in claim 1.

3. The thickening stabilizer composition comprising a miscible material of the thickening stabilizer described in claim 2 and a fluid organic substance.

4. A method for manufacturing a thickening stabilizer composition, the method comprising blending the thickening stabilizer described in claim 2 and a fluid organic substance to make a miscible material to produce a thickening stabilizer composition.

* * * * *